United States Patent [19]

Long et al.

[11] Patent Number: 4,718,026

[45] Date of Patent: Jan. 5, 1988

[54] MONITORING SHEET MATERIAL

[75] Inventors: Terence M. Long; David J. Newman; Peter D. Thomas, all of Bristol, England

[73] Assignee: Imperial Group, PLC, London, England

[21] Appl. No.: 614,171

[22] Filed: May 25, 1984

[51] Int. Cl.[4] ...................... G06F 15/20; G06F 15/353
[52] U.S. Cl. .................................... 364/550; 250/339; 364/498
[58] Field of Search .................. 364/550, 498, 471; 356/51, 319, 320, 346; 250/339

[56] References Cited

U.S. PATENT DOCUMENTS

| | | | |
|---|---|---|---|
| 3,793,524 | 2/1974 | Howarth | 250/339 |
| 3,851,175 | 11/1974 | Dahlin et al. | 250/339 |
| 4,267,572 | 5/1981 | Witte | 364/498 |
| 4,299,487 | 11/1981 | Sengoku et al. | 356/320 |
| 4,363,968 | 12/1982 | McGowan et al. | 250/339 |
| 4,455,084 | 6/1984 | Webb, Jr. et al. | 364/498 |

FOREIGN PATENT DOCUMENTS

| | | |
|---|---|---|
| 1039746 | 8/1966 | United Kingdom . |
| 1069910 | 5/1967 | United Kingdom . |
| 1126841 | 9/1968 | United Kingdom . |
| 2008745 | 6/1979 | United Kingdom . |

Primary Examiner—Felix D. Gruber
Assistant Examiner—H. R. Herndon
Attorney, Agent, or Firm—Cushman, Darby & Cushman

[57] ABSTRACT

Inorganic constituents of cigarette paper are identified and monitored by scanning a region of the infra red spectrum of the paper, computing first and second order derivatives of the scan, comparing the first and second order derivatives by a best fit comparison with reference spectral data, and computing concentrations in the paper of the identified inorganic constituents.

5 Claims, 5 Drawing Figures

CARBONATE PROCESS    FIG. 3
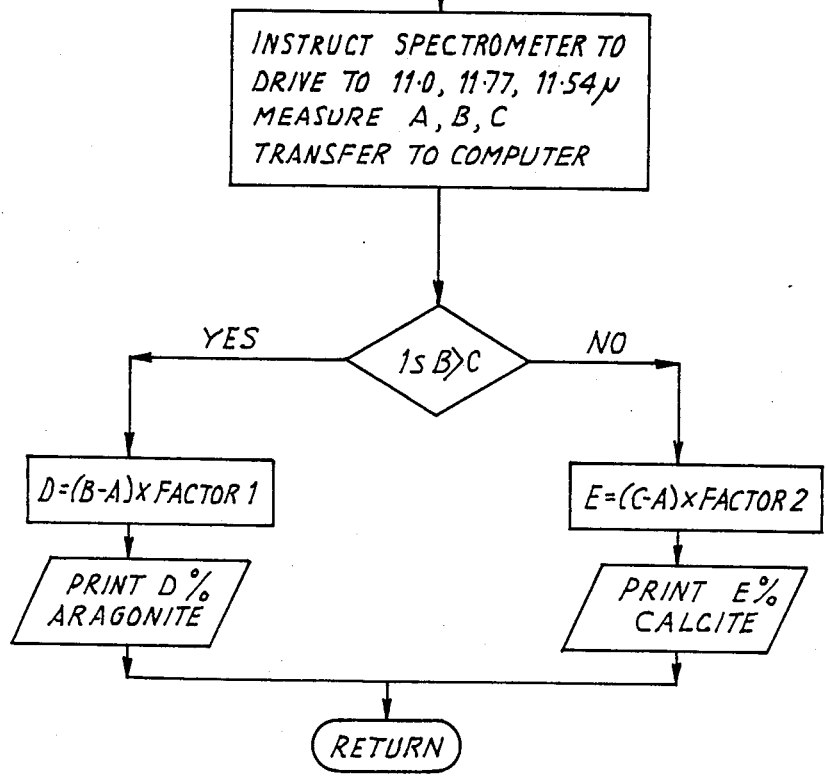
CITRATE PROCESS    FIG. 4
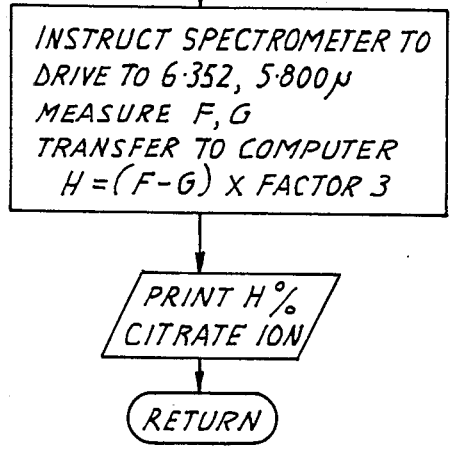

MONITORING SHEET MATERIAL

BACKGROUND OF THE INVENTION

This invention relates to improvements in or relating to the monitoring of constituents of sheet material, in particular the on-line monitoring of additive constituents of cigarette paper.

It is customary in research and development work in the tobacco industry to measure a number of cigarette paper additives such as calcium carbonate, sodium, potassium, magnesium and mixed sodium and potassium citrates, and monoammonium and disodium phosphate. It is for instance commonplace in research and development experiments to analyze paper before making and before smoking in order to minimize retests.

Calcium carbonate is a filler and affects air permeability and burn rate of cigarette paper, while citrates affect burn rate and phosphates affect ash characteristics. In many research and development applications values of citrate and carbonate are among the most requested analytical data.

Carbonate is currently analyzed by acid/base titration or carbonate electrode. Citrate is analyzed by pyridine/acetic anhydride reaction or by using permanganate titration or metal analysis methods. Most methods thus measure the anion only and additive weight percentage is calculated using assumed cations.

It is seen that there is a need for a rapid automated system for paper additives analysis with immediate feedback of results and portability for siting in areas where fast data feedback can be used most effectively.

SUMMARY OF THE INVENTION

According to a first aspect of the present invention there is provided a method of monitoring on-line the concentration of a selected additive in a web of sheet material comprising selecting a first wavelength at which the infra red absorbance of the additive is at a maximum, selecting a second wavelength at which the infra red absorbance of the additive is at a minimum, measuring the infra red optical density of the material at the first wavelength and generating a first signal indicative of the optical density at the first wavelength, measuring the infra red optical density of the material at the second wavelength and generating a second signal indicative of the optical density at the second wavelength, determining the difference between the first and second signals and computing from said difference the concentration of the additive in the material.

According to a second aspect of the present invention there is provided a method of identifying and monitoring a constituent in a material comprising selecting and scanning a region of the infra red spectrum of the material, computing first and second order derivatives of the scan, comparing the first and second order derivatives by a best fit comparison with reference infra red spectral data of known constituents thereby identifying said constituent and determining its concentration in the material.

According to a third aspect of the present invention there is provided an apparatus for monitoring on-line the concentration of a selected additive in a web of sheet material, the apparatus comprising in combination means for measuring the optical densities of the additive at first and second selected wavelengths at which the infra red absorbance of the additive is respectively at a maximum and a minimum, meant for generating first and second signals corresponding to said optical densities, means for determining the difference between the first and second signals, and means for computing from said difference the concentration of the additive in the material.

According to a fourth aspect of the present invention there is provided an apparatus for identifying and monitoring a selected constituent of a material, the apparatus comprising in combination means for scanning a selected region of the infra red spectrum, and means to compute first and second derivatives of the scan, to compare said first and second order derivatives by a best fit comparison with reference infra red spectral data, and means to determine therefrom the concentration of said constituent in the material.

The invention will now be described by way of example only with reference to the accompanying drawings.

BRIEF DESCRIPTION OF THE DRAWINGS

FIGS. 1–4 are flow charts depicting the method and apparatus of the present invention and FIG. 5 is a schematic representation of an apparatus in accordance with the present invention.

DETAILED DESCRIPTION OF THE PRESENTLY PREFERRED EXEMPLARY EMBODIMENT

Figure 1:
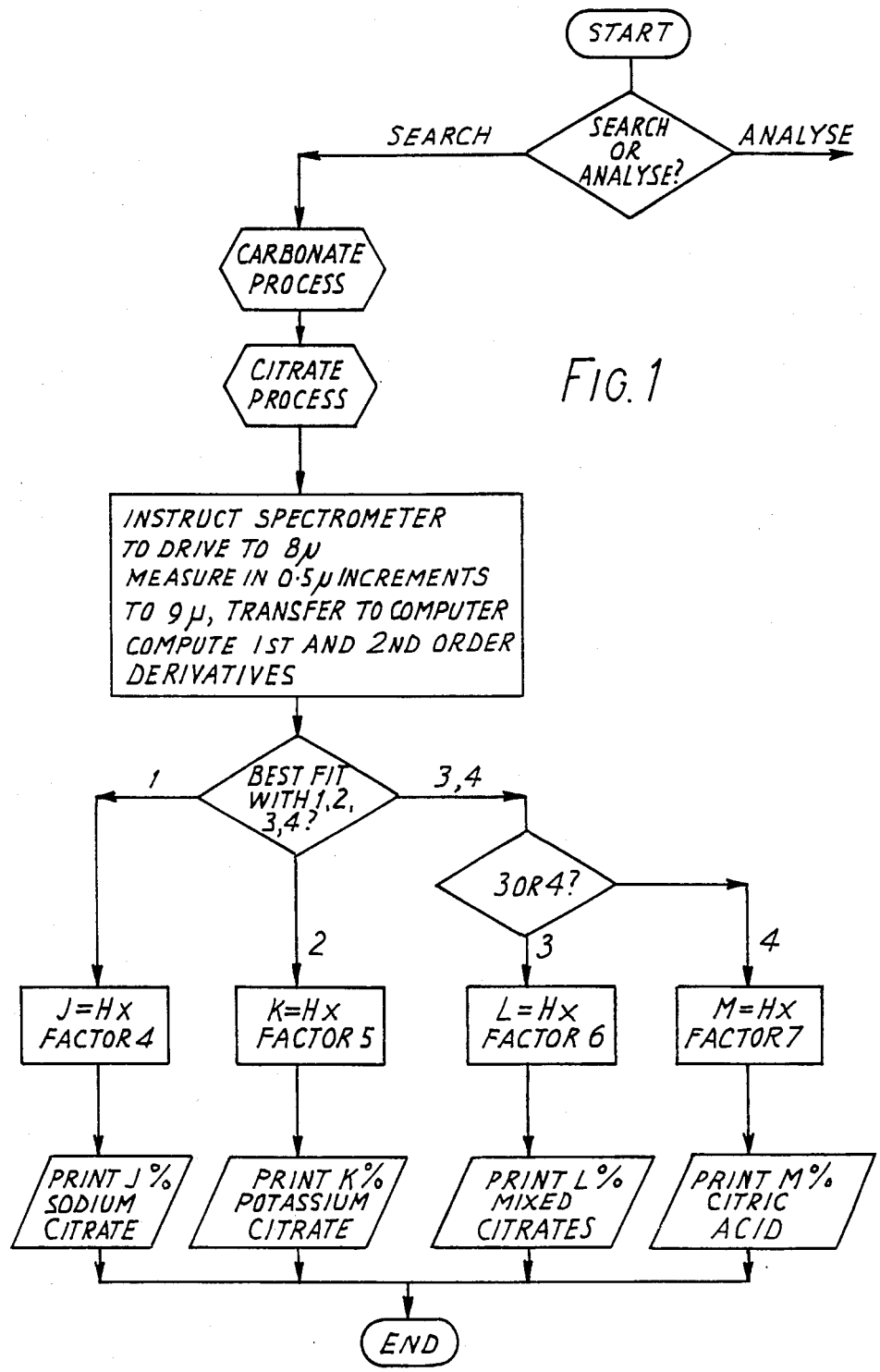

The method of monitoring according to the invention is applied to cigarette paper analysis as a series of operations in which the additive anions are determined by their characteristic fundamental infra red absorptions, and the cation component, or the physical structure (e.g., crystalline structure), of the additive is identified by complex pattern recognition of the spectral find structure. The anion is then measured by the method of the invention and the additive weight percentage is calculated with reference to the identified cation. The sequential steps and specific instructions to the spectrometer are processed automatically by an interfaced computer, which also interprets the spectral data and outputs the desired information on the number of additives, their percentage loading and, where appropriate, their respective physical structures.

Preliminary tests indicated that the citrate and carbonate ions gave characteristic peaks in the mid-infra red region of the spectrum which were reasonably free from interference by other paper constituents. A quantitative infra red analyzer, the Miran 80 (Trade Mark), was used a a central unit for analysis of cigarette paper additives in the examples.

The Miran 80 is a single beam infra red spectrometer with a spectral range of 2.5 to 14.5 microns controlled by a dedicated microprocessor; (1 micron=0.000001 m and is indicated in the drawings by the Greek letter "mu"). The instrument can be used qualitatively linked to a recorder to provide analog infra red scans, or digital scans using the inbuilt printer. This particular instrument is able to analyze up to a maximum of 11 components directly from liquid, solid, or gaseous mixtures, without the necessity for prior separation before analysis.

Peak maxima of the relevant infra red absorbances are selected from the literature and by running short digital scans over the areas of interest in the infra red spectrum of the mixture. The wavelengths of these peak maxima are then stored in the microprocessor together with a reference wavelength (i.e., a point in the spectrum where little or no absorbance occurs). The spectrometer measures optical densities at each of these wavelengths and converts them via a programmed matrix to concentration. Parameters such as analysis time per wavelength and delay between repeat analyses may be varied to give the optimum optical density reading.

Calibration is carried out by measuring the optical density at the selected wavelengths of samples of known concentration. An external computer program then converts the values of optical density and concentration to a matrix suitable for the Miran 80, using linear matrix algebra. It is convenient to use a program that cn give either zero or non-zero intercepts on request.

When the matrix and parameters have been entered into the microprocessor, analyses may be carried out automatically at the press of a button.

Paper from a single cigarette may simply be clamped in a sample holder and exposed to the beam of light from the spectrometer. Alternatively, large reels of paper may be run through the light path while the instrument is analyzing.

EXAMPLE 1

Determination of calcium carbonate

Calcium carbonate occurs in two crystalline forms, namely aragonite (rhombic), and calcite (ditrigonal), both of which are used in cigarette paper manufacture. Their main infra red spectral maxima of 6.90 and 11.77 microns, for aragonite, and 7.14 and 11.54 microns for calcite are due to doubly degenerate asymmetric stretching and out-of-plane bending of the carbonate ion respectively.

The mid infra red spectrum of cigarette paper is dominated by its major constituent, that is, cellulose.

Its variable absorption at 6-8 microns precludes using the major carbonate peaks of 6.90 and 7.14 microns, so consequently the chosen analytical wavelength for paper analysis is the out-of-plane bending at 11.77 (aragonite) or 11.54 and 11.8 microns will show the crystalline form present if the source is unknown. The reference wavelength used is 11.00 microns which is the minimum between a cellulose absorption and the out-of-plane bending of the carbonate ion, and is independent of crystal structure.

The zero and gain of the spectrometer were set prior to calibration using a chalk-free paper. The spectrometer was then calibrated using three papers previously analyzed by acid/base titration and covering the range 5.9 to 29.9% by weight aragonite in approximately equal steps.

Table 1 shows the carbonate content of various papers obtained by the analysis technique of the invention and compared with analytical results obtained by a reference titrimetric procedure. Where a substantial anomaly was noticed the paper concerned was analysed again using a thermogravimetric technique. Such anomalies are believed to be due to the fact that reference values were determined on averages of approximately 2 meter lengths of paper, whereas infra red data and data obtained by thermogravimetric techniques were determined on 0.01 m lengths of paper.

EXAMPLE 2

Determination of citrate ion

Cellulose and carbonate absorptions combine to give relatively few infra red transparent "windows" for citrate measurement, and there is only one peak in the citrate ion infra red spectrum that stands out from the normal paper background at low levels. This is at 6.352 microns and is due to asymmetric stretch of the strongly coupled carbon and oxygens of the acid functional groups. The absorption of this peak is dependent on the cation associated with the citrate ion and is greater for a monovalent cation than for a divalent cation at the same level of citrate ion. The enhancement follows a linear relationship and so may be compensated for in the off line matrix program. Two wavelengths are required for the analysis. The analytical wavelength at 6.352 microns, and the reference wavelength, a minimum between cellulose and citrate absorbance, at 5.800 microns.

The zero and gain of the spectrometer were set prior to calibration using a non-citrate paper. The spectrometer was then calibrated using two papers containing 2.08 and 3.95% by weight citrate ion, added a citric acid and therefore present in the paper as calcium citrate. The citrate levels had previously been determined using the pyridine/acetic ahydride reaction.

Table 2 shows the citrate content of various papers obtained by the analysis technique of the invention and compared with analytical results obtained by a reference titrimeric procedure.

A regression analysis carried out on the date of Table 2 gave the following equation:

$$\text{spectrometer} = 1.2728 \times \text{titrimetric method} + 0.018$$

That is, the citrate absorbance for sodium and potassium salts is 1.273 times greater than that of calcium citrate (the product of adding citric acid to chalk loaded paper, in samples 21 and 22).

The enhancement effect of monovalent cations was confirmed by standard additions of potassium citrate, sodium citrate and citric acid to base paper. Additions were calculated to give 10% citrate ion concentrations on the paper. Results are given in Table 3, where measured citrate refers to measurements made by the method of the spectrometer, and corrected citrates are those values divided by 1.273.

Each citrate measurement made by the method of the invention using the spectrometer was taken over approximately 0.004 m paper, the width of the infra red incident beam. This gives the technique sufficient discrimination to measure short or long term distribution trends.

It is found by the method of the invention that cigarette paper can be analyzed for carbonate and citrate content rapidly, automatically, and on line, without destroying or otherwise harming the paper.

An outline of the controlling computer program is described as follows, first in general terms, and then with specific reference to the flow charts shown in FIGS. 1 to 4.

The operator is presented with the choice of a full additives search and analysis or specific analysis of a known additive. Selection of the search routine will instruct the spectrometer to scan aragonite and calcite absorptions, identify the type, and to analyze and report the percentage loading.

The spectrometer is then instructed by the computer to scan the main citrate peak and, if citrate is detected, to measure the percentage citrate and then to scan the spectral region between 8.0 and 9.0 microns in 20 equal increments. These data are used to compute second derivatives at 8.70, 8.75, and 8.82 microns by a best fit technique using the central-difference formula given in "Interpolation and Allied Tables", HMSO, 1956, using four observations either side of each point. The spectra of pure sodium, potassium and calcium citrates can be characterized by a minor absorbance peak at 8.70 microns for sodium citrate, 8.75 microns for potassium citrate, and 8.82 microns for calcium citrate. In cigarette paper they occur as inflexions on a major peak at 8.50 microns but are resolved by the second derivative analysis described above. The presence of sodium citrate is confirmed by a minimum second derivative at 8.70 microns, potassium citrate is confirmed by a minimum value at 8.82 microns. Similarly, the presence of mixed citrates is confirmed by minima at both 8.70 and 8.75 microns. From these identifications of the cation associated with citrate, the additive loading is computed and reported.

Selection of the analyze option requests the operation to enter the full identity of the additive. The spectrometer is then instructed to scan the appropriate fraction of the infra red spectrum; spectral values are converted to a percentage loading and final values are reported.

The use of first and second derivatives of the scan is a sensitive technique for identifying and measuring peaks that are close to and masked by another peak or peaks.

The invention is now described with specific reference to the flow charts of FIGS. 1 to 4.

With reference to FIG. 1 the user is invited to choose either the search or the analyze option. FIG. 1 then proceeds with the search option by carrying out the "carbonate process" which is shown in more detail in FIG. 3.

In the carbonate process of FIG. 3 the computer instructs the spectrometer to measure the peaks at 11.0, 11.77, and 11.54 microns. The heights of the peaks at these wavelengths are A, B, and C, respectively. The computer then works out the percentages D and E of aragonite and calcite respectively from the formulae, $$D=(B-A)\times \text{factor 1}$$
$$E=(C-A)\times \text{factor 2}$$

where factor 1 and factor 2 are constants peculiar to the apparatus and which have to be determined by calibration.

Having determined the carbonate content by the process of FIG. 3 we now return to FIG. 1 and proceed with the "citrate process" which is shown in more detail in FIG. 4.

In the citrate process of FIG. 4 the computer instructs the spectrometer to measure the peaks at 6.352 and 5.800 microns. The heights of these peaks at these wavelengths are F and G respectively. The computer then works out the percentage H of the citrate ion from the formula, $$H=(F-G)\times \text{factor 3}$$

where factor 3 is a constant peculiar to the apparatus and which has to be determined by clibration.

Having determined the citrate ion content by the process of FIG. 4 we return yet again to FIG. 1 and proceed with the process of determining the ion to be associated with the citrate ion, i.e., sodium, potassium, sodium/potassium mixture, calcium or hydrogen (i.e., citric acid).

This is done by instructing the spectrometer to drive to 8.0 microns and to measure the peaks over the range 8-9 microns in 0.5 micron increments. The results are tested in the manner described above for the best statistical fit with the appropriate ion. If the best fit is with sodium we multiply H by factor 4 to obtain J, the percentage of sodium citrate. Likewise, if the best fit is with any of the three other possibilities we multiply H by any one of factors 5-7 to obtain the respective percentage K, L or M of potassium citrate, mixed citrates, or citric acid, as appropriate.

Factors 4-7 are the ratios for converting the percentage of citrate ion to sodium citrate, potassium citrate, mixed citrates, or citric acid respectively.

| The values of factors 4-7 are, |
|---|
| factor 4 = 1.366 |
| factor 5 = 1.621 |
| factor 6 = 1.493 |
| factor 7 = 1.0158 |

Figure 2:
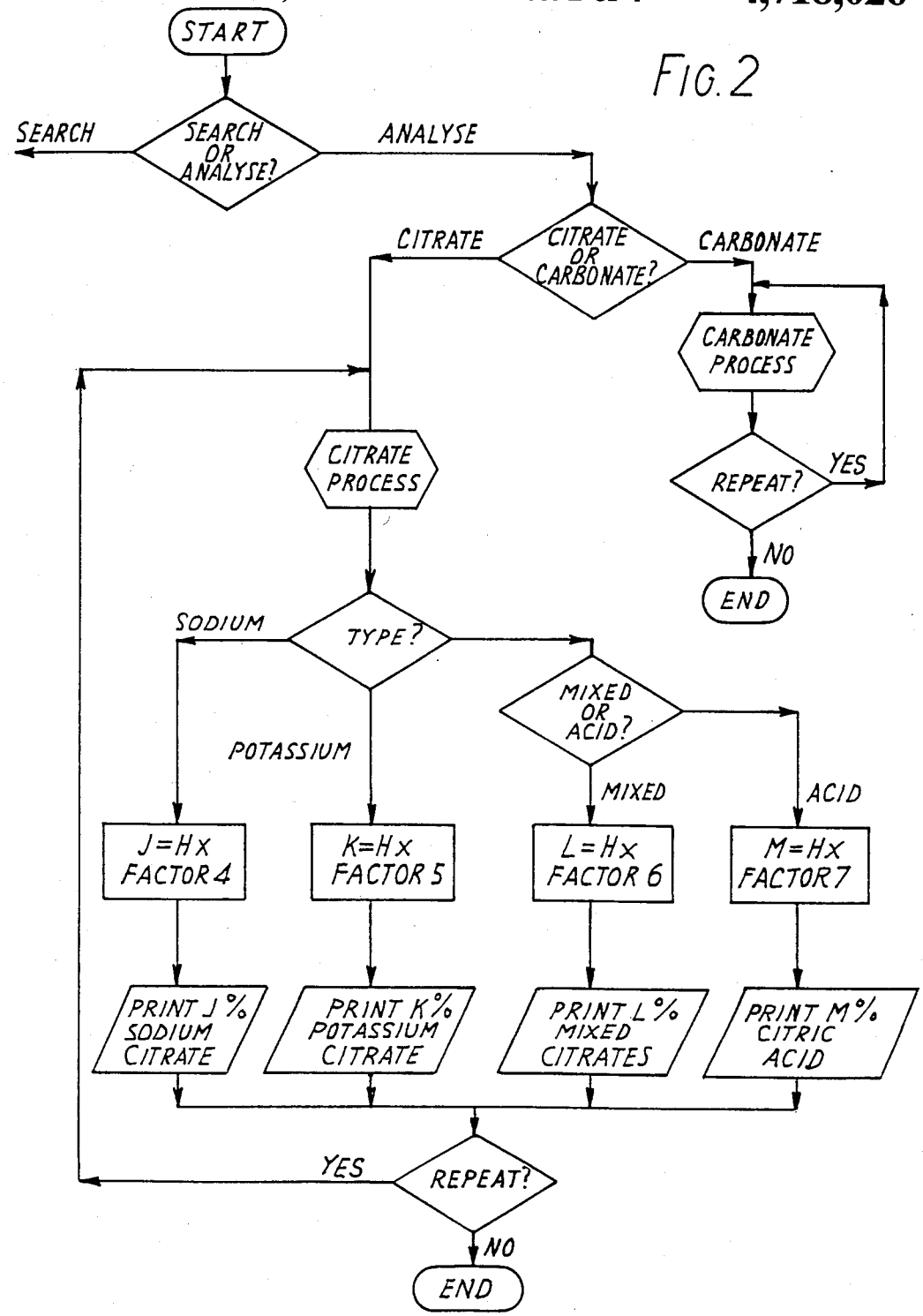

FIG. 2 is similar in detail to FIG. 1 but illustrates instead the option of analyzing for a single substance, i.e., citrate or carbonate, and if citrate, then the choice of sodium citrate, potassium citrate, mixed citrates, or citric acid. The "carbonate" and "citrate" possesses are the same as described with reference to FIGS. 3 and 4 respectively, and factors 4-7 have the same values as listed above.

It will be understood that the technique of implementing the flow charts shown in FIGS. 1 to 4 on a computer is well known in the computing art and need not be described in this specification.

The method of the invention is particularly useful for analyzing the constituents of cigarette paper because cigarette paper is characterized by an even thickness and smooth surface. The method of the invention may clearly be adapted to other papers having similar properties, such as banknote paper or the like.

The method of the invention may be used to identify or to measure other constituents of cigarette paper on line, such as the identification of the form of mineral chalk or the cation associated with citrate. The form or source of the cellulose constituent of the paper may also be characterized.

The invention may also be used to analyze plug or plugwrap constituents or to analyze flavours.

The invention may also be used in paper making process control.

Figure 5:
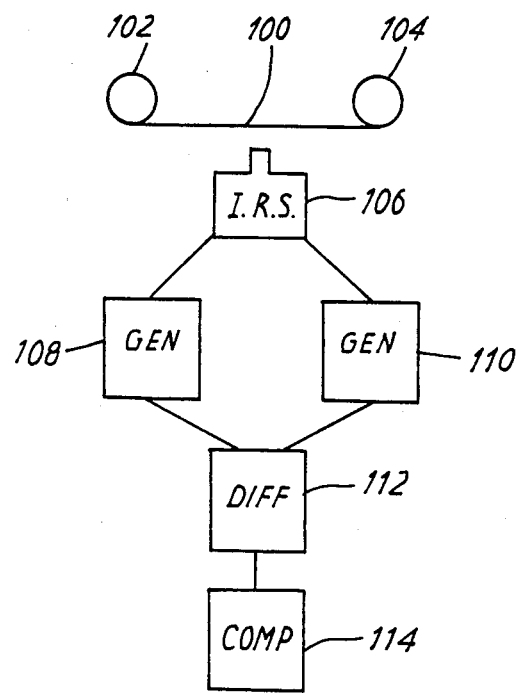

FIG. 5 is a schematic representation of apparatus embodying the invention. A web 100 of sheet material, e.g., paper is moved by means of reels 102, 140 past an infra-red spectrometer 106, e.g., a Miran 80 as described above. This scans a selected spectral region and measures the optical densities, determined by additive in the web material, at first and second wavelengths at which the infra-red absorption of the additive is at a maximum and a minimum respectively. Signals corresponding to the densities are fed to means 108, 110 for generating corresponding signals, which are fed to means 112 for determining their difference. A resulting output signal passes to computing means 114 which calculates from it the concentration of the additive in the material.

TABLE 1

| Sample No. | Reference Titration | Spectrometer | Thermogravimetry |
|---|---|---|---|
| 1 | 28.5 | 28.4 | |
| 2 | 35.0 | 37.8 | 37.5 |
| 3 | 11.4 | 12.1 | |
| 4 | 19.4 | 18.9 | |
| 5 | 22.7 | 19.7 | 20.5 |

TABLE 1-continued

| Sample No. | Reference Titration | Spectrometer | Thermogravimetry |
|---|---|---|---|
| 6 | 15.9 | 14.1 | 14.2 |
| 7 | 54.8 | 45.5 | 50.0 |
| 8 | 27.3 | 26.3 | |
| 9 | 25.0 | 22.6 | 24.7 |
| 10 | 25.6 | 22.3 | 25.6 |
| 11 | 23.3 | 12.1 | 12.8 |
| 12 | 27.4 | 27.5 | |
| 13 | 26.1 | 22.7 | 25.0 |
| 14 | 27.2 | 28.6 | |

TABLE 3

| Cation | Measured citrate | Corrected citrate |
|---|---|---|
| K+ | 12.0 | 9.4 |
| NA+ | 12.9 | 10.1 |
| H+(Ca) | 9.8 | — |

TABLE 2

| Sample No. | Reference Titration | Spectrometer | Type of citrate |
|---|---|---|---|
| 1 | 0.32 | 0.41 | 100% K |
| 2 | 0.71 | 0.97 | 100% K |
| 3 | 1.11 | 1.34 | 100% K |
| 4 | 1.50 | 1.92 | 100% K |
| 5 | 0.42 | 0.41 | 100% Na |
| 6 | 0.88 | 1.28 | 100% Na |
| 7 | 1.33 | 1.99 | 100% Na |
| 8 | 1.66 | 2.12 | 100% Na |
| 9 | 0.37 | 0.68 | 25% Na:75% K |
| 10 | 0.38 | 0.63 | 50% Na:50% K |
| 11 | 0.40 | 0.58 | 75% Na:25% K |
| 12 | 0.74 | 0.90 | 25% Na:75% K |
| 13 | 0.78 | 1.05 | 50% Na:50% K |
| 14 | 0.82 | 1.20 | 75% Na:25% K |
| 15 | 1.13 | 1.06 | 25% Na:75% K |
| 16 | 1.16 | 1.55 | 50% Na:50% K |
| 17 | 1.21 | 1.64 | 75% Na:25% K |
| 18 | 1.53 | 2.05 | 25% Na:75% K |
| 19 | 1.64 | 1.87 | 50% Na:50% K |
| 20 | 1.68 | 1.95 | 75% Na:25% K |
| 21 | 2.15 | 2.15 | 100% Citric Acid |
| 22 | 2.28 | 2.31 | 100% Citric Acid |

What is claimed is:

1. A method for measuring on-line the concentration of an additive selected from the group consisting of calcium carbonate, sodium citrate, potassium citrate and calcium citrate in a web of cigarette paper, the method comprising the steps of:

passing first and second beams of radiation at respective first and second wavelengths in the mid-infra red spectral range through the web, the first and second wavelengths being wavelengths at which the infra red absorbance of the additive is at a maximum and a minimum, respectively, measuring the infra red optical densities of the web at the first and second wavelengths, and generating first and second signals indicative of the respective optical densities at the first and second wavelengths, the difference between the first and second signals being indicative of the concentration of the additive in the web.

2. A method as claimed in claim 1, for further identifying a said additive in the web and measuring the concentration of said additive in the web, further comprising the steps of:

scanning successive wavelengths in a selected region of said infra red spectral range of the web and generating scan data, measuring the infra red optical density of the web at each of said successive wavelengths, determining with a computer means first and second order derivatives of the scan data over said selected region, and comparing the first and second order derivatives by a best fit comparison with reference infra red spectral data of known additives, thereby identifying said additive and determining its concentration in the web.

3. A method as claimed in claim 2, wherein the additive comprises an anion and a cation, and wherein said step of determining comprises determining the anion by its characteristic fundamental infra red adsorption and determining the cation by complex pattern recognition of the infra red spectral fine structure.

4. An apparatus for measuring on-line the concentration of an additive selected from the group consisting of calciumm carbonate, sodium citrate, potassium citrate, and calcium citrate in a web of cigarette paper, the apparatus comprising, in combination, means for measuring the optical densities of the additive at first and second selected wavelengths in the mid-infra red range of the spectrum, at which the infra red adsorption of the additive is respectfully at a maximum and a minimum, means for generating first and second signals corresponding to said optical densities, means for determining the difference between the first and second signals, and means for computing from said difference the concentration of the additive in the web.

5. An apparatus as claimed in claim 4, for identifying and measuring a said selected additive in the web, the apparatus further comprising, in combination:

means for scanning the web at successive wavelengths in a selected region of said range of the infra red spectrum and generating scan data, means for measuring the infra red optical density of the web at each of said successive wavelengths, computer means to derive first and second order derivatives of the scan data over said selected region.

computer means to compare said first and second order derivatives by a best fit comparison with reference infra red spectral data, and computer means to determine therefrom the concentration of said additive in the web.

* * * * *